United States Patent [19]

Grade et al.

[11] 4,304,590
[45] Dec. 8, 1981

[54] METHODS AND COMPOSITIONS FOR THE CONTROL OF HARMFUL ORGANISMS CONTAINING ALIPHATIC PRIMARY DIAMINES

[75] Inventors: Reinhardt Grade; Joachim Lorenz, both of Bensheim, Fed. Rep. of Germany; René Muntwyler, Hofstetten; Heinz Peter, Rheinfelden, both of Switzerland

[73] Assignee: Ciba-Geigy Corporation, Ardsley, N.Y.

[21] Appl. No.: 116,140

[22] Filed: Jan. 28, 1980

[30] Foreign Application Priority Data

Sep. 2, 1979 [CH] Switzerland .......................... 1294/79

[51] Int. Cl.³ .......................................... A01N 33/02
[52] U.S. Cl. .......................................... 71/67; 424/325
[58] Field of Search .............................. 424/325; 71/67

[56] References Cited

U.S. PATENT DOCUMENTS

| | | | |
|---|---|---|---|
| 2,246,524 | 6/1941 | Kyrides | 424/325 |
| 3,064,052 | 11/1962 | Goldberg et al. | 424/325 |
| 3,139,376 | 6/1964 | Gilbert | 424/325 |
| 4,100,111 | 7/1978 | Peter et al. | 528/116 |

FOREIGN PATENT DOCUMENTS

| | | | |
|---|---|---|---|
| 4174108 | 8/1979 | Japan | 424/325 |
| 7313354 | 3/1974 | Netherlands | 424/325 |
| 1419339 | 12/1975 | United Kingdom . | |

*Primary Examiner*—Douglas W. Robinson
*Attorney, Agent, or Firm*—Harry Falber

[57] ABSTRACT

The invention relates to the use of diamines of the formula I

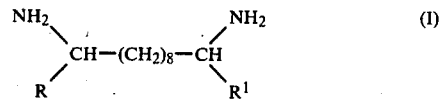

in which R and $R^1$ are, for example, identical and are alkyl, as active substances for the control of harmful organisms in water and other materials, especially industrial materials. Inter alia, bacteria, fungi, yeasts and algae are controlled.

The control is effected in standing and running waters. In preservatives and disinfectants, the diamines are used for natural and synthetic materials, especially industrial materials.

8 Claims, No Drawings

METHODS AND COMPOSITIONS FOR THE CONTROL OF HARMFUL ORGANISMS CONTAINING ALIPHATIC PRIMARY DIAMINES

The invention relates to the use of aliphatic primary diamines as active substances for the control of harmful organisms in aqueous and non-aqueous systems.

The use of aliphatic primary mono- and di-amines, and especially of so-called fatty amines, such as coconut fatty amine or dodecylamine, as active substances against bacteria, fungi, algae or the like has already been described several times in the literature.

In this context, reference should be made to the following publications: A. Simek et al. "Antimicrobially active substances", Folia Microbiologica 14, 508–510 (1969), H. J. Hueck et al. "Bacteriostatic, fungistatic, and algistatic activity of fatty nitrogen compounds", Appl. Microbiology 14, 308–319 (1966) and A. T. Fuller "Anti-bacterial action and chemical constitution in long-chain aliphatic bases", Biochem J. 36, 548–558 (1942).

German Pat. No. 2,247,369 should also be mentioned as further prior art. In German Patent Specification No. 2,247,369 the use of compounds of the formula

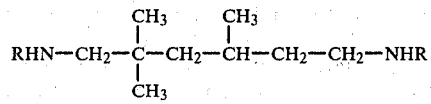

which contain a primary amino group and in which one R is a hydrogen radical and the other R is a dodecyl radical or a mixture of alkyl radicals (average $C_{12}H_{25}$—), as microbiocidal active substances is claimed.

However, all of the previously disclosed aliphatic substances containing at least one primary amino group which have a biological activity have the disadvantage that their microbiocidal activity is too low. Gram-positive and Gram-negative bacteria are destroyed to only an inadequate extent.

The object of the invention is to find an aliphatic substance, containing primary amino groups, for the control of harmful substances, which substances not only has a good biostatic activity but at the same time is an outstanding microbiocidal active substance. This substance should be more suitable for destroying Gram-positive and Gram-negative bacteria than the active amines which are employed according to methods of the indicated prior art.

The invention relates to a method for the control of harmful organisms in water and on materials which contain water or are virtually anhydrous, by mixing aliphatic primary amines, as active substances, into the water or material to be protected, or by applying the aliphatic primary amines to the surface of the material to be protected, which comprises using, as the active substance, an amine of the formula (I)

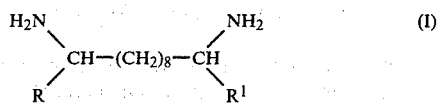

in which R and $R^1$ are identical or different and are each a straight-chain or branched alkyl radical having a total of 1 to 14 carbon atoms or a cycloalkyl radical which has a total of 3 to 12 carbon atoms and can be substituted by alkyl.

According to the invention, it is possible to use both the free diamines of the formula I and the salts thereof with, for example, the inorganic or organic acids listed below: hydrochloric acid, phosphoric acid, phosphorous acid, carbonic acid, sulfuric acid, sulfurous acid, acetic acid, citric acid and formic acid.

The mixing in, according to the invention, of the diamines of the formula I is to be understood as meaning in the main the dissolving and/or emulsifying of the diamines in the water or material to be protected. In specific cases, however, the procedure can also be to add the particular diamine in an amount which is larger than that which is required per se for dissolving and/or emulsifying, or to add the diamine very carefully, so that accelerated dissolving or emulsifying is initially avoided. The effect of procedures of this type is that particles of large volume or large drops are also present in the material to be protected. This can be advantageous when it is important that the diamines have a depot effect.

The diamines used according to the invention are highly effective against the most important harmful organisms and in particular against harmful microorganisms. Examples of specific organisms which are controllable by the method according to the invention are: bacteria, fungi, yeasts and algae, but also the balanidae and serpulidae found in seawater.

The diamines of the formula I which are used according to the invention can be combined with virtually all of the commonly used antimicrobally active substances, in some cases with the utilisation of synergistic effects. Preferred categories of substances for combination are compounds such as quaternary ammonium, phosphonium and sulfonium salts, other amines, ureas, phenols, aldehydes, carboxylic acids, tributyl-tin oxide and its derivatives, N-oxides, peroxides, sulfides, disulfides, carbamates, carboxamides, which can be substituted by halogen, mercapto compounds, such as mercaptothiadiazoles and 2-mercapto-pyridine 1-oxide and its Na salt and Zn salt, and dihalogenonitriloacetic acid amides, iodine compounds, chlorohexidine and iso- and benziso-thiazolone derivatives.

In order to make use of synergism, the compounds contained according to the invention in the preservatives and disinfectants can also be combined with acid, neutral or basic salts and buffers.

In particular for the control of harmful organisms in cooling water, it is possible at the same time to add further conventional assistants to the diamines of the formula I when these are used according to the invention, for example corrosion inhibitors, agents which prevent boiler scale, agents for softening the water, masking agents, for example polymeric phosphites, phosphates, amides of phosphoric acid, phosphonic acids, polymeric carboxylic acids of, for example, acrylic acid or maleic acid, their anhydrides or salts, and other additives.

With the method according to the invention, the diamines of the formula I can also be added or applied in the form of liquid, pasty or solid preparations (compositions). Such preparations can be, for example, suspensions, emulsions and solutions in organic or inorganic solvents. In antimicrobially active preparations, the substances to be used according to the invention are employed in amounts of 0.1 to 10 percent by weight and preferably of 0.5 to 5 percent by weight.

The preparations can, of course, additionally also contain active substances commonly used against harmful organisms, especially the known antimicrobially active substances already mentioned above. The same applies in the case of the abovementioned basic salts and buffers and also in the case of the cooling water assistants.

In general, the following assistants in particular are required to prepare the compositions or preparations used against harmful substances: carriers, extenders, emulsifiers, humectants, fixing agents and interface-active compounds. The carriers are solid or liquid carriers, such as clay, kaolin, talc, diatomaceous earth, silica, calcium carbonate, benzene, alcohols, xylene, methylnaphthalene, dimethylformamide, diethylsulfoxide, animal and vegetable oils, fatty acids and their esters and diverse interface-active compounds.

A preferred embodiment of the invention is a method (A), which comprises the control of harmful organisms in water or in aqueous solutions and dispersions with an amine of the formula (I) in which R in each case is the same as $R^1$ and is a straight-chain or branched alkyl radical having a total of 1 to 14 carbon atoms or a cycloalkyl radical which has a total of 3 to 11 carbon atoms and can be substituted by alkyl.

This method (A) is particularly effective when an amine of the formula (I) is employed in which R is a straight-chain alkyl radical or a cycloalkyl radical having, in each case, 5 to 8 carbon atoms and is preferably a straight-chain alkyl radical having 6 to 8 C atoms.

A particular embodiment of method (A) comprises carrying out the control of the harmful organisms by dissolving and/or emulsifying the amine of the formula (I) in the water or the aqueous system in a concentration of 0.05 to 300 ppm and preferably of 0.1 to 50 ppm, based on the water.

Another advantageous embodiment of method (A) comprises the control of the harmful organisms in the main at the interface between plastic bodies or coats of protective paint, especially coats of antifouling paint, located in the water, and the water, by employing those plastic bodies or protective paints into which the amine of the formula (I) has been mixed, the concentration of the amine of the formula (I) being 0.01 to 10 and preferably 0.1 to 5 percent by weight, based on the plastic or the protective paint.

The effect of such a procedure is that these plastic bodies and also the actual structural components of concrete, tiles, wood, metal or the like which are to be protected and to which these plastics or protective paints have been applied, are protected against the accumulation of organisms from seawater or against the deposition of slimes which can be formed by microorganisms of all types. At the same time, the protective effect can also extend to the entire water. The active effect of the diamine of the formula I is thus not necessarily restricted to the interface between the plastic bodies or protective paints and the water.

Such plastic bodies, which are exposed to water, are preferably pipes, valves, taps, plates and films, the latter being in particular those used for lining water containers or basins, or also water basins or containers. The plastics are preferably polyolefins, such as polyethylene or polypropylene, polystyrene, polyvinyl chloride, unsaturated polyester resins, synthetic or natural rubbers or polycarbonates and polyfluorocarbones.

Protective paints used for method (A) are in particular antifouling paints which contain, as base materials, the lacquer raw materials which are customarily termed binders and are known to those skilled in the art. These are, in particular, polyvinyl chloride, polyvinylidene chloride, polystyrene, polyvinyltoluene, polyvinyl esters, polyacrylates, polymethacrylates and corresponding esters, and also copolymers thereof, and also SB and ABS polymers, synthetic and natural rubber (which can be chlorinated or cyclised), polyurethanes, epoxide resins and unsaturated polyester resins. The use of such antifouling paints for the method according to the invention is a further preferred embodiment of the invention.

The control of harmful organisms by method (A) can also be carried out very effectively by not only dissolving and/or emulsifying the amine of the formula (I) in the water or aqueous system but, at the same time, using in the water plastic bodies or protective paints into which the amine of the formula (I) has been mixed.

Method (A) according to the invention is preferably used for the control of harmful organisms in standing and running waters, such as swimming pools and ponds, and especially in cooling water cycles and water cycles and also in the paper industry; the said waters can be either fresh water or seawater.

Method (A) also includes the control of harmful organisms in aqueous dispersions. These are to be understood as meaning, inter alia, molecularly disperse (i.e. true) salt solutions, for example the seawater already mentioned and cooling water which has a high salt content and is suitable for cooling to below 0° C. Further dispersions of this type are also suspensions and emulsions such as are sometimes obtained in industry.

The content of dissolved or dispersed solids and/or non-aqueous liquids in the aqueous solutions and dispersions in which harmful organisms can be controlled by method (A) is in general restricted to not more than 10% by weight, based on the solution or dispersion.

The diamines of the formula I are stable to the effects of pH, so that the method according to the invention can be carried out at virtually all possible pH values.

A further preferred embodiment of the invention is a method (B), which comprises using the amines of the formula (I) for the control of micro-organisms and preferably for protecting natural, synthetic and in particular industrial materials against attack by micro-organisms, R and $R^1$ in the formula (I) being, in each case, a straight-chain or branched alkyl radical having a total of 1 to 12 carbon atoms or a cycloalkyl radical which has a total of 5 to 12 carbon atoms, of which not more than 5 to 8 are ring-forming carbon atoms, and can be substituted by alkyl.

The amines of the formula I preferably employed for this method (B) are those in which R is the same as $R^1$ and R is preferably a straight-chain or branched alkyl radical having a total of 4 to 8 carbon atoms or a cycloalkyl radical having 5 to 8 carbon atoms in the ring.

The materials to be protected by method (B) can also contain water. However, the water content is in general restricted to not more than 95% by weight, based on the total material.

The use, according to the invention, of the diamines of the formula I by method (B) is on the one hand effected by mixing the said diamines into the material to be protected in a concentration of 10 to 2,000 ppm, based on the material to be protected without any water which may be present, or by dissolving and/or emulsifying the said diamines in the said material. Industrial solutions and dispersions (suspensions and emulsions), for example, can be preserved in this way. The said solutions and dispersions are, for example, formulated agricultural chemicals and paints in cans or canisters, sizes, starch pastes and cutting and drilling oils.

Method (B) according to the invention can also be used particularly effectively in the paper and cellulose industry. In this case it is in particular the troublesome formation of slime, which can arise on the paper and cellulose pulps, and also on apparatus used in the paper industry and is caused by micro-organisms, which is controlled.

Another way in which the active diamines are used according to method (B) is in the form of a surface disinfection of solid bodies, especially of walls, floors and the like. Examples of materials of this type to be protected are wood, bamboo, plastics, stone and brickwork, textiles and leather and in the latter cases it is in general not only a surface effect but a total impregnation which results. This surface disinfection is of particular importance in abattoirs, foodstuff factories and breweries. The surface disinfection is carried out by spraying, painting, sprinkling or saturating the articles or surfaces with formulations containing the active diamines and in particular with corresponding aqueous or non-aqueous solutions. Advantageously, the concentration of active amines of the formula I in these formulations is so chosen that, after the treatment, the amount of active amines finally present on the surfaces is 0.1 to 10 g/m$^2$.

The invention also relates to compositions for the control of harmful organisms in water or in aqueous solutions and dispersions, containing, as the active substance, an amine of the formula I in which R and R$^1$ are in each case identical and are a straight-chain or branched alkyl radical having a total of 1 to 14 C atoms or a cycloalkyl radical which has a total of 3 to 11 C atoms and can be substituted by alkyl, the concentration of the amine of the formula I being 0.1 to 10 and preferably 0.5 to 5% by weight, based on the total composition.

Preferably, these compositions contain an amine of the formula (I) in which R and R$^1$ are each a straight-chain alkyl radical or a cycloalkyl radical, each having 5 to 8 carbon atoms, and preferably a n-alkyl radical having 6 to 8 C atoms.

As already mentioned above, the compositions according to the invention can also contain other active substances commonly used against harmful organisms, and further assistants.

The invention also relates to plastic bodies and linings, in particular pipes, sheets, films, valves and taps (or corresponding plugs, of cocks or taps, and inserts), containers and basins, which are preferably intended for use in water and for the control of harmful substances in water, into which plastic bodies and linings an amine of the formula I, in which R and R$^1$ are identical in each case and are a straight-chain or branched alkyl radical having a total of 1 to 14 C atoms or a cycloalkyl radical which has a total of 3 to 11 C atoms and can be substituted by alkyl, has been mixed in a concentration of 0.01 to 10 and preferably 0.1 to 5% by weight, based on the total plastic body.

The invention also relates to antifouling paints for underwater paintwork, containing an amine of the formula I which is active against harmful substances and in which R and R$^1$ are identical in each case and are a straight-chain or branched alkyl radical having a total of 1 to 14 C atoms or a cycloalkyl radical which has a total of 3 to 11 C atoms and can be substituted by alkyl, in a concentration of 0.01 to 30 and preferably 0.1 to 10% by weight, based on the total antifouling paint.

The invention also relates to compositions, for the control of micro-organisms, containing a diamine of the formula I, in which R and R$^1$ are identical or different and are each a straight-chain or branched alkyl radical having a total of 1 to 12 C atoms or a cycloalkyl radical which has a total of 5 to 12 C atoms, of which not more than 5 to 8 are ring-forming C atoms, and can be substituted by alkyl, in a concentration of 0.1 to 10 and preferably 0.5 to 5% by weight, based on the total composition.

Preferably, these compositions contain a diamine of the formula I in which R and R$^1$ are identical in each case.

Preferred amines of the formula I are those in which R is a straight-chain or branched alkyl radical having a total of 4 to 8 C atoms or a cycloalkyl radical having 5 to 8 C atoms in the ring.

The diamines of the formula I which are used according to the invention can be prepared, for example, analogously to the process described in U.S. Pat. No. 4,100,111, by catalytic hydrogenation of 1,2-diaza-1,5,9-cyclododecatrienes or corresponding 1,2-diaza-1-cyclododecenes.

Examples of specific compounds of the formula I are: 1,10-diamino-1,10-dicyclohexyldecane, prepared according to Example 1 of U.S. Pat. No. 4,100,111; 1,10-diamino-1,10-dicyclopentyldecane; prepared by catalytic hydrogenation of 3,12-dicyclopentyl-1,2-diaza-1,5,9-cyclododecatriene; colourless oil: boiling point 174°–178° C./0.26 Pa; n$_D^{20}$=1.4885; IR (liquid) bands at, inter alia, 3,355, 3,278 and 1,613 cm$^{-1}$; 3,12-diamino-2,13-dimethyltetradecane, prepared according to Example 3 of U.S. Pat. No. 4,100,111; 6,15-diaminoeicosane, prepared by catalytic hydrogenation of 3,12-di-n-pentyl-1,2-diaza-cyclododecene (mixture of diastereomers), colourless oil: boiling point 167°–170° C./0.13 Pa; n$_D^{20}$=1.4603; IR (liquid ) bands at, inter alia, 3,378, 3,289 and 1,613 cm$^{-1}$; 4,13-diamino-3,14-diethylhexadecane, prepared by catalytic hydrogenation of 3,12-di-(3-pentyl)-1,2-diazacyclododecene; colourless oil; boiling point 141°–143° C./0.5 Pa; n$_D^{20}$=1.4666; IR (liquid) bands at, inter alia, 3,378, 3,278 and 1,613 cm$^{-1}$; 7,16-diaminodocosane, prepared by catalytic hydrogenation of 3,12-dihexyl-1,2-diazacyclododecene (mixture of diastereomers); colourless oil; boiling point 184° C./2.6 to 0.7 Pa; n$_{D1}^{20}$=1.4624; IR (liquid) bands at, inter alia, 3,355, 3,278 and 1.613 cm$^{-1}$; 8,17-diaminotetracosane, prepared according to Example 7 of U.S. Pat. No. 4,100,111; 6,15-diamino-5,16-diethyleicosane, prepared by catalytic hydrogenation of 3,12-di-(3-heptyl)-1,2-diazacyclododecene (mixture of diastereomers); colourless oil; boiling point 170° C./1.3 Pa; n$_{D1}^{20}$=1.4662; IR (liquid) bands at, inter alia, 3,278 and 1,613 cm$^{-1}$; 9,18-diaminohexacosane, prepared by cataytic hydrogenation of 3,12-di-n-octyl-1,2-diaza-1,5,9-cyclododecatriene (mixture of diastereomers); colourless oil; 10,19-di-aminooctacosane, prepared by catalytic hydrogenation of 3,12-di-n-nonyl-1,2-diaza-1,5,9-cyclododecatriene (mixture of diastereomers); melting point 33°–37° C.; IR (CH$_2$Cl$_2$) bands at, inter alia, 3,225 and 1,582 cm$^{-1}$; 11,20-diaminotriacontane, prepared by catalytic hydrogenation of 3,12-di-n-decyl-1,2-diaza-1,5,9-cyclododecatriene; 3,12-diaminotetradecane, colourless oil (boiling point 83° to 85° C./0.7 Pa); 4,13-diaminohexadecane, colourless oil (boiling point 132°-135° C./0.01 mm Hg); 5,14-diaminooctadecane, colourless oil (boiling point 149° C./0.001 mm Hg); 4,13-diamino-3,14-dimethylhexadecane, colourless oil (boiling point 143°-145° C./7 Pa); 4,13-diamino-2,15-dimethylhexadecane, colourless oil (boiling point 168°-172° C./0.04 mm Hg); 12,21-diaminodotriacontane, melting point 45° to 46° C., and 13,22-diaminotetratriacontane.

The last 7 products listed are also prepared by catalytic hydrogenation of corresponding 1,2-diaza-1,5,9-cyclododecatrienes.

The 1,2-diaza-1,5,9-cyclododecatrienes and 1,2-diazacyclododecenes used as starting materials are prepared by the processes described in U.S. Pat. Nos. 3,939,147 and 4,100,111.

EXAMPLES

(I.) Method (A)

EXAMPLE 1 TO 13

(Determination of the minimum inhibitory concentration against bacteria). The ONC's (cultures cultivated overnight) of the various strains of bacteria: 1 Escherichia coli, 13 Proteus vulgaris, 7 Pseudomonas aeruginosa, 10 Enterobacter aerogenes, 8 Serratia marcenscens, 11 Alcaligenes denitrificans, 2 Bacillus subtilis, 20 Streptomyces griseus and 6 Staphylococcus aureus, grown in caso-peptone broth (Merck) are each diluted 1/1,000 in saline. The suspensions are added to caso-peptone broth in an amount such that the bacteria are again diluted 1/100. The diamines of the formula I which are listed in Table 1 and in which R in each case is the same as $R^1$ are then added in amounts of 5, 10, 30, 100 and 300 mg/l to each sample dilution. After a cultivation period of 24 hours at 30° C. in a shaking waterbath, the samples are assessed to determine any turbidity. The minimum inhibitory concentration (MIC) is the concentration at which the broth does not become turbid as a result of bacterial growth. The result is illustrated in Table 1 below.

6 *Staphylococcus aureus*
7 *Pseudomonas aeruginosa*
8 *Serratia marcescens*
10 *Enterobacter aerogenes*
11 *Alcaligenes denitrificans*
13 *Proteus vulgaris*
19 *Streptomyces aureofasciculus*
20 *Streptomyces griseus* and
27 *Pseudomonas oleovorans* grown in caso-peptone broth, are each diluted 1/100 in saline. The suspensions are added to saline or Ringer's solution in amounts such that the bacteria in the mixture are each diluted 1/1,000.

The diamine of the formula I, in which R and $R^1$ are each n-heptyl, is then added in an amount such that the concentration of the diamine is 1, 2, 4, 6, 8, 10, 15, 20, 25 or 30 mg/l in each case. For comparison, the same procedure is carried out using coconut fatty amine.

After a cultivation period of 24 hours at 30° C. in a shaking waterbath, 10 μl are taken from the sample and added dropwise to caso-peptone agar. After a further cultivation period of 24 hours at 30° C., the samples are checked visually to determine if there is any growth. In Table 2 below + signifies growth on the agar plate and − signifies no growth and thus destruction of the bacteria in the buffer solution.

TABLE 2

Determination of the concentration required for destruction of the mixed culture of bacteria

| Concentration (mg/l) | 8,17-Diamino-tetracosane | Coconut fatty amine for comparison |
|---|---|---|
| 1 | + | + |
| 2 | (+) | + |
| 4 | − | + |
| 6 | − | + |
| 8 | − | + |
| 10 | − | (+) |
| 15 | − | − |
| 20 | − | − |
| 25 | − | − |
| 30 | − | − |

TABLE 1

Determination of the MIC of the diamines (concentration tested: 5, 10, 30, 100 and 300 mg/l)

| Example | R and $R^1$ in formula I | Strains | | | | | | | |
|---|---|---|---|---|---|---|---|---|---|
| | | 1 | 2 | 6 | 7 | 8 | 10 | 11 | 13 | 20 |
| 1 | ethyl | 300 | >100 | >100 | >300 | >300 | >300 | >300 | >300 | 100 |
| 2 | n-propyl | 100 | 100 | >100 | >300 | >300 | 300 | 300 | 300 | 100 |
| 3 | n-butyl | ≦30 | 30 | 30 | >300 | 300 | 100 | 100 | 100 | 10 |
| 4 | i-butyl | 100 | 30 | 100 | >300 | >300 | 100 | 100 | 300 | 30 |
| 5 | n-pentyl | ≦10 | <5 | ≦5 | 100 | 100 | ≦10 | ≦10 | <10 | ≦5 |
| 6 | n-hexyl | ≦5 | ≦5 | ≦5 | 30 | 10 | ≦5 | ≦5 | ≦5 | ≦5 |
| 7 | cyclohexyl | ≦10 | ≦5 | 10 | 100 | 100 | 30 | 30 | 30 | ≦5 |
| 8 | n-heptyl | ≦5 | ≦5 | ≦5 | ≦5 | ≦5 | ≦5 | ≦5 | ≦5 | ≦5 |
| 9 | 3-heptyl | ≦5 | ≦5 | ≦5 | 30 | 100 | 10 | 30 | 30 | ≦5 |
| 10 | n-octyl | ≦5 | ≦5 | ≦5 | 10 | ≦5 | ≦5 | ≦5 | ≦5 | ≦5 |
| 11 | cyclooctyl | ≦5 | ≦5 | ≦5 | 30 | 10 | ≦5 | 10 | ≦5 | ≦5 |
| 12 | n-nonyl | ≦10 | ≦5 | ≦5 | >300 | ≦10 | ≦10 | ≦10 | ≦10 | ≦5 |
| 13 | n-decyl | ≦10 | ≦5 | ≦5 | >300 | 300 | 300 | 300 | ≦10 | ≦5 |

The high growth-inhibiting action of the diamines against the various bacteria can be seen from Table 1.

EXAMPLE 14

(Determination of the minimum concentration for destruction in 24 hours when 8,17-diaminotetracosane is used.) The UNC's of the various strains of bacteria:
1 *Escherichia coil*
2 *Bacillus subtilis*
4 *Bacillus cereus var. mycoides*

The outstanding action of 8,17-diaminotetracosane in destruction of the bacteria can be seen from Table 2.

In order to destroy a mixed culture of the 12 bacteria in Ringer's solution or saline 4 ppm of the diamine are required and 15 ppm (3-4×) of coconut fatty amine are required.

EXAMPLES 15 to 18

Example 18=comparison example) (Determination of the minimum concentration of diamines of the formula I and of laurylamine required for destruction over various periods of time.)

In order to prepare the mixed culture, the UNC's of the various strains of bacteria:

1 *Escherichia coli*
4 *Bacillus cereus* var. *mycoides*
6 *Staphylococcus aureus*
7 *Pseudomonas aeruginosa*
10 *Enterobacter aerogenes* and
13 *Proteus vulgaris* grown in caso-peptone broth, are each added to saline in an amount such that a final dilution of 1/1,000 is obtained.

After various times of treatment with the particular biocide at 30° C. in a shaking waterbath, the germ count is determined by means of diluting, removing with a spatula and cultivating again.

Table 3 shows the course of destruction as a function of time for 3 diamines used according to the invention, which are in the minimum concentration required for destruction within 6 hours, and gives a comparison with the action of laurylamine.

The following diamines are tested:

EXAMPLE 15

9,18-diaminohexacosane (minimum concentration 2 ppm)

EXAMPLE 16

8,17-diaminotetracosane (minimum concentration 2 ppm)

EXAMPLE 17

7,16-diaminodocosane (minimum concentration 5 ppm)

EXAMPLE 18

(comparison) laurylamine (concentration used: 10 ppm)

The surprisingly powerful destructive action of the diamines of the formula I can clearly be seen from the table. When the diamines of the formula I are used in the indicated concentration, 2 to 6 hours suffice for destruction of the mixed culture, whilst 10 ppm of laurylamine are not sufficient to effect destruction within 12 hours.

TABLE 3

Determination of the germ count after various periods of treatment with 4 different amines in saline.

| Example | Concentration mg/l | Time elapsed after addition of the biocide, hours | Germ count/ml |
|---|---|---|---|
| 15 | 2 | 1 | $5 \times 10^3$ |
|  |  | 2.5 | $1 \times 10^3$ |
|  |  | 5.5 | $1 \times 10^2$ |
|  |  | 8.5 | $4 \times 10^2$ |
| 16 | 2 | 1 | $8 \times 10^3$ |
|  |  | 2.5 | $<10^2$ |
|  |  | 5.5 | $<10^2$ |
|  |  | 8.5 | $<10^2$ |
| 17 | 5 | 1 | $4 \times 10^6$ |
|  |  | 2.5 | $1 \times 10^5$ |
|  |  | 5.5 | $1 \times 10^2$ |
|  |  | 8.5 | $<10^2$ |
| 18 | 10 | 1 | $2 \times 10^7$ |
|  |  | 2.5 | $2 \times 10^7$ |
|  |  | 5.5 | $1 \times 10^7$ |
|  |  | 8.5 | $1 \times 10^7$ |

Control 0 minutes after addition of the biocide $4 \times 10^7$ germs/ml.

EXAMPLES 19 to 22

(Determination of the minimum inhibitory concentration of diamines of the formula I against algae)

The cultures of the various strains of algae: *Oscillatoria geminata, Nostoc spez., Phormidium foveolarum, Anacystis nidulans, Chlorella vulgaris, Chlorella pyrenoidosa, Scenedesmus spec., Ulothrix subtilissima* and *Tribonema aequale*, grown for 14 days in nutrient medium for algae, are diluted 1/200 in nutrient medium for algae, in order to prepare the mixed culture. The diamines of the formula I listed in Table 4 are then each added in amounts such that concentrations of 1, 3, 10 and 30 mg/l result. After a cultivation period of 14 days at 18° C. in a shaker, the samples are assessed visually to determine the growth. Table 4 shows the particular concentration of the various diamines which is required to inhibit the growth of the mixed culture of algae.

TABLE 4

| Example | $R = R^1$ in formula I | Concentration (mg/l) |
|---|---|---|
| 19 | n-butyl | 10 |
| 20 | n-hexyl | 1 |
| 21 | n-octyl | 10 |
| 22 | cyclooctyl | 3 |

EXAMPLES 23 to 32

(Determination of the minimum inhibitory concentration of the diamines used according to the invention, against fungi.)

The experiment is carried out by the known agar incorporation test using the fungi
CA = *Candida albicans*
TM = *Trichophyton mentagrophytes*
AN = *Aspergillus niger*
PF = *Penicillium funiculosum*
AA = *Alternaria alternata*.

For inhibition, various diamines of the formula I are each added in amounts such that concentrations of 3, 10, 30, 100 and 300 mg/l result.

The particular minimum concentration (mg/l) required for inhibition is shown in Table 5.

TABLE 5

| Example | $R = R^1$ in formula I | Fungi | | | | |
|---|---|---|---|---|---|---|
| | | CA | TM | AN | PF | AA |
| 23 | ethyl | 300 | >300 | >300 | 100 | >300 |
| 24 | n-butyl | 100 | 100 | 100 | 10 | 100 |
| 25 | n-pentyl | 30 | 30 | 30 | 3 | 10 |
| 26 | n-hexyl | 10 | 10 | 30 | 3 | 10 |
| 27 | n-heptyl | 10 | 10 | 30 | 3 | 3 |
| 28 | 3-heptyl | 10 | 10 | 30 | 10 | |
| 29 | n-octyl | 30 | 30 | 100 | 30 | |
| 30 | cyclooctyl | 10 | 10 | 100 | 10 | |
| 31 | n-nonyl | 300 | 100 | 300 | 30 | 10 |
| 32 | n-decyl | >300 | 300 | >300 | 300 | 100 |

The test results shown in Tables 4 and 5 indicate the high effectiveness of the diamines used according to the invention against algae and fungi also.

(II.) Method (B)

EXAMPLES 33 to 54

The test to determine the bactericidal and fungicidal activity of the active substances listed below by the suspension test is given below.

A phosphate buffer medium (pH 5.7 and 8), which contains 1,000, 100, 10, 1 or 0.1 ppm of the active amine of the formula I in each case, is inoculated with, in each case, one test strain (bacteria: O/n cultures, fungi: spore suspension 14 day cultures) (final concentration $10^6$ germs/ml). After an incubation period of 18 hours at 20° C. over a magnetic stirrer, the samples are checked to determine at which concentrations destruction of the germs has taken place. The compounds tested show an excellent germicidal action in this test.

| | |
|---|---|
| Staphylococcus aureus | ATCC 6538 |
| Escherichia coli | ATCC 11229 |
| Pseudomonas aeruginosa | ATCC 15442 |
| Aspergillus niger | ATCC 6275 |

Medium: Sörenson phosphate buffer (1/15 molar) with 2% of brain-heart infusion broth.

The diamines of the formula I used are the following substances.

| Example | R = R$^1$ in formula I | Active amine |
|---|---|---|
| 33 | methyl | 2,11-diaminododecane |
| 34 | ethyl | 3,12-diaminotetradecane |
| 35 | n-propyl | 4,13-diaminohexadecane |
| 36 | i-propyl | 3,12-diamino-2,13-dimethyltetradecane |
| 37 | n-butyl | 5,14-diaminooctadecane |
| 38 | 2-butyl | 4,13-diamino-3,14-dimethylhexadecane |
| 39 | isobutyl | 4,13-diamino-2,15-dimethylhexadecane |
| 40 | n-pentyl | 6,15-diaminoeicosane |
| 41 | cyclopentyl | 1,10-diamino-1,10-dicyclopentyldecane |
| 42 | 3-pentyl | 4,13-diamino-3,14-diethylhexadecane |
| 43 | n-hexyl | 7,16-diaminodocosane |
| 44 | cyclohexyl | 1,10-diamino-1,10-dicyclohexyldecane |
| 45 | n-heptyl | 8,17-diaminotetracosane |
| 46 | 3-heptyl | 6,15-diamino-5,16-diethyleicosane |
| 47 | cycloheptyl | 1,10-diamino-1,10-dicycloheptyldecane |
| 48 | n-octyl | 9,18-diaminohexacosane |
| 49 | 4-octyl | 6,15-diamino-5,16-dipropyleicosane |
| 50 | cyclooctyl | 1,10-diamino-1,10-dicyclooctyldecane |
| 51 | n-nonyl | 10,19-diaminooctacosane |
| 52 | n-decyl | 11,20-diaminotriacontane |
| 53 | undecyl | 12,21-diaminodotriacontane |
| 54 | dodecyl | 13,22-tetratriacontane |

EXAMPLES 55 to 76

In the following examples, the same active diamines of the formula I as in Examples 33 to 54 are tested by the agar incorporation test to determine the bacteriostatic and fungistatic action.

A 5% stock solution in methylcellosolve is prepared from each of the test compounds. This stock solution is used to prepare a dilution series such that the concentrations in the individual solutions each differ by a power of ten. 0.3 ml samples of each of the solutions thus obtained are placed in sterile Petri dishes and each sample is mixed with 15 ml of a hot, liquid nutrient medium (nutrient agar). The nutrient medium then contains 1,000, 100, 10, 1 or 0.1 ppm of active amine.

After the plates have solidified, the particular germ suspensions (the germs used were the same as those in Examples 33 to 54) are added dropwise to these plates using a Pasteur pipette or using the inoculation apparatus. The incubation time for bacteria is 24 hours at 37° C. and for Aspergillus niger is 3 days at 28° C. After this time an assessment is made to determine up to which concentration of active substance the germs have grown. All 22 compounds tested display a bacteriostatic and fungistatic action towards the germs tested.

EXAMPLE 77

The diamines of the formula I are dissolved in a suitable formulation (ethylcellosolve/dimethylformamide). The three substrates listed below are placed in the formulation baths and then squeezed off between 2 aluminium foils and then air-dried. Squeezing is carried out in such a way that there are 1,000 ppm of active substance on the fabric.

1. Strengthened cotton, causticised and bleached, weight per m$^2$: 121 g
2. Polyamide, nylon staple fabric, fixed and bleached, weight per m$^2$: 140 g
3. Polyester, Dacron staple fabric, type 54, fixed and bleached, weight per m$^2$: 130 g.

The substrates are then tested against the 7 test organisms listed below using the agar diffusion test (modified ATCC test method 90, 1970).

| | |
|---|---|
| Bacteria: | |
| Staphylococcus aureus | ATCC 6538 |
| Escherichia coli | · NCTC 8196 |
| Proteus mirabilis | NCTC 8309 |
| Pseudomonas aeruginosa | NCTC 8060 |
| Fungi: | |
| Candida albicans | ATCC 10259 |
| Trichophyton mentagrophytes | ATCC 9533 |
| Aspergillus niger | ATCC 6275 |

The test plates consisting of a two-layer agar, i.e. of a base layer of nutrient agar which has not been inoculated and a top layer of inoculated nutrient agar (nutrient agar for bacteria; Mycophil agar, fungi). The filtered germ suspension is poured onto a solidified base layer and after the inoculated layer has solidified 20 mm diameter discs of the treated substrates are placed on this layer. The bacteria and Candida plates are cultivated for 24 hours at 37° C. and the fungi plates are incubated for 3 to 5 days at 28° C. After incubation, the plates are assessed in respect of inhibiting zones. If there are no inhibiting zones, the growth beneath the test disc is checked under a microscope.

The diamines tested in this way show, in combination with the substrates used, a good action against the bacteria and fungi used.

EXAMPLE 78

An emulsifiable concentrate is prepared by mixing the following constituents: 10 parts by weight of a 1,10- diaminoalkane of the formula I, 68 parts by weight of xylene, 10 parts by weight of dimethylformamide and 12 parts by weight of an interfaceactive compound.

Before use, the concentrate is diluted with water to 50 to 200 times the amount. Wood or sawdust is saturated in the emulsion thus obtained and by this means are protected against attack by bacteria and fungi.

EXAMPLE 79

An oil-soluble concentrate is prepared by mixing the following constituents: 20 parts by weight of a 1,10-diaminoalkane of the formula I, 40 parts by weight of ethylene glycol monoethyl ether, 10 parts by weight of dimethylformamide and 30 parts by weight of xylene.

The resulting concentrate is mixed into a paint or a cutting oil in an amount such that the paint or the oil contains 0.1 percent by weight of diamine. Protection against attack by bacteria and fungi is achieved in this way.

EXAMPLE 80

Use in antifouling paints

The compound, according to the invention, of the formula I in which R and $R^1$ are n-octyl was tested in two different antifouling paints A and B. The first paint (A) is a chlorinated rubber antifouling paint which contained the compound to be tested as the sole antifouling additive in a concentration of 28.5% by volume of the total solids. In the second antifouling paint (B), which was based on a vinyl chloride copolymer with colophony as the binder, the compound to be tested was likewise used in a concentration of 28.5% by volume of the total solids. The antifouling paints were made up as follows:

|  | Parts by weight |
|---|---|
| A | |
| chlorinated rubber, type 10 | 71 |
| plasticiser (Clophen A 60) | 6 |
| epoxidised soya bean oil | 2 |
| talc | 32 |
| red iron oxide | 55 |
| barytes | 50 |
| white petroleum spirit rich in aromatics | 115 |
| butyl acetate | 7 |
| xylene | 115 |
| B | |
| vinyl chloride/acetate resin (91% VC, 3% VAC, 6% BA) | 41 |
| colophony | 14 |
| tris-tolyl phosphate | 7 |
| epoxidised soya bean oil | 2 |
| talc | 32 |
| red iron oxide | 55 |
| barytes | 50 |
| MIBK | 79 |
| xylene | 83 |

The antifouling paints A and B were applied to prepared test plates in a coating thickness of about 60μ (plate preparation: steel plates, sand-blasted, vinyl butyral primer and red lead oxide anticorrosive paint, a red lead oxide, based on chlorinated rubber being prepared for the chlorinated rubber antifouling paint and a red lead oxide based on vinyl chloride copolymer being prepared for the other antifouling paint). For testing under conditions encountered in practice, the plates were exposed on a test station in the Mediterranean at which very extensive coverage with growth due to marine organisms takes place.

Evaluation

Evaluation is in accordance with a numerical grading scheme, in which 0 signifies complete coverage with growth and 10 signifies complete absence of growth. The numbers 1-9 then correspond to a gradual grading of the intensity of coverage with growth. The test was carried out during the growth period from mid June to the end of February of the following year. In this region, coverage with growth due, in particular, to polychaete worms (Serpulidae) and acorn barnacles (Balanidae) takes place during this period. The following results were obtained:

Paint sample A
front side 9, back 7, mainly Serpulidae
Paint sample B
front side 8, back 2, growth in the main Balanidae.

EXAMPLE 81

Test to determine the effectiveness in model circulation systems

Test description:

The following compounds were tested, to determine their slime-preventing action, in model circulation systems which were located on the roof (natural irradiation by the sun, open to dust, weathering influences) and consisted of a plastic tub and a cooling tower, which was made of diverse materials and through which water was circulated by means of a pump: coconut fatty amine, the compound of the formula I in which R and $R^1$ are n-hexyl and the compound of the formula I in which R and $R^1$ are n-heptyl.

The feed of fresh water was adjusted so that the losses due to splashing and evaporation were compensated and the biocides were diluted approximately 1:2 in the course of one week. Prior to each addition of the biocide, which was carried out once per week, inoculation with the following cultures was carried out:

1. 14-day old algae cultures of
   *Oscillatoria geminata*
   *Nostoc* spez.
   *Phormidium foveolarum*
   *Anacylstis nidulans*
   *Chlorella vulgaris*
   *Chlorella pyrenoidosa*
   *Scenedsmus* spec.
   *Ulothrix subtilissima*
   *Tribonema aequale*
2. ONC's of each of the following strains of bacteria:
   *Bacillus cereus* var. *mycoides*
   *Bacillus subtilis*
   *Streptomyces griseus*
   *Staphylococcus aureus*
   *Pseudomonas aeruginosa*
   *Enterobacter aerogenes*
   *Serratia marcescens*
   *Alcaligenes Denitrificans*
   *Escherichia coli*
   *Proteus vulgaris*

The test period was 8 weeks.

The amines tested in this way displayed an outstanding action. Even in concentrations which do not have an inhibitory effect on the growth of bacteria in the system (for example due to the continuous feed of fresh water), not only the diamine of the formula I in which R and $R^1$ are n-hexyl but also the diamine of the formula I in which R and $R^1$ are n-heptyl prevent the formation of slime, whilst in the untreated circulation systems and in the circulation systems treated with coconut fatty amine growth of algae and slime formation take place.

What is claimed is:

1. A method for combatting harmful bacterial, fungus, yeast or algae organisms in water, aqueous and non-aqueous dispersions and solutions, and on solid substrates which comprises mixing into the aqueous or non-aqueous material to be protected, or applying to the surface of the solid material to be protected, a microbiocidally effective amount of an amine of the formula (I)

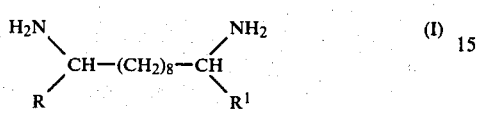

in which R and R¹ are identical or different and are each a straight-chain or branched alkyl radical having a total of 1 to 14 carbon atoms or a cycloalkyl radical which can be substituted by alkyl and which has a total of 3 to 12 carbon atoms.

2. The method of claim 1 for combatting said organisms in water or in aqueous solutions and dispersions wherein R in each case is the same as R¹ and is a straight-chain or branched alkyl radical having a total of 1 to 14 carbon atoms or a cycloalkyl radical which can be substituted by alkyl and which has a total of 3 to 11 carbon atoms.

3. The method of claim 2, wherein an amine of the formula (I) is employed in which R is a straight-chain alkyl radical having 6 to 8 carbon atoms.

4. The method of claim 1, wherein said active substance is applied to the surface of the material to be protected and wherein R and R¹ in the formula (I) are, in each case, a straight-chain or branched alkyl radical having a total of 1 to 12 carbon atoms or a cycloalkyl radical which can be substituted by alkyl and which has a total of 5 to 12 carbon atoms, of which not more than 5 to 8 are ring-forming carbon atoms.

5. The method of claim 4, wherein amines of the formula (I) are employed in which R and R¹ are identical.

6. The method of claim 5, wherein an amine of the formula (I) is employed in which R is a straight-chain or branched alkyl radical having a total of 4 to 8 carbon atoms or a cycloalkyl radical having 5 to 8 carbon atoms in the ring.

7. A composition for combatting harmful bacterial, fungus, yeast or algae organisms in water or in aqueous solutions and dispersions containing, as the active substance, an amine of the formula I

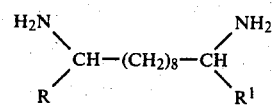

wherein R and R¹ are in each case identical and are a straight-chain or branched alkyl radical having a total of 1 to 14 C atoms or a cycloalkyl radical which can be substituted by alkyl and which has a total of 3 to 11 C atoms, the concentration of the amine of the formula I being 0.1 to 10 percent by weight, based on the total composition, together with a suitable pesticide carrier therefor.

8. A composition for combatting harmful bacterial, fungus, yeast or algae organisms containing, as the active substance, a diamine of the formula I

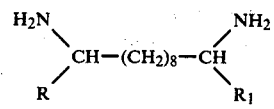

wherein R and R¹ are identical or different and are each a straight-chain or branched alkyl radical having a total of 1 to 12 C atoms or a cycloalkyl radical which can be substituted by alkyl and which has a total of 5 to 12 C atoms, of which not more than 5 to 8 are ring-forming C atoms, in a concentration of 0.1 to 10 percent by weight, based on the total composition, together with a suitable pesticide carrier therefor.

* * * * *